(12) United States Patent
Yamashita et al.

(10) Patent No.: US 8,785,008 B2
(45) Date of Patent: Jul. 22, 2014

(54) ZIRCONIA SINTERED BODIES WITH HIGH TOTAL LIGHT TRANSMISSION AND HIGH STRENGTH, USES OF THE SAME, AND PROCESS FOR PRODUCING THE SAME

(75) Inventors: Isao Yamashita, Kanagawa (JP); Koji Tsukuma, Kanagawa (JP); Toru Tsuyoshi, Kanagawa (JP)

(73) Assignee: Tosoh Corporation, Shunan-shi (JP)

( * ) Notice: Subject to any disclaimer, the term of this patent is extended or adjusted under 35 U.S.C. 154(b) by 654 days.

(21) Appl. No.: 12/375,001

(22) PCT Filed: Jul. 19, 2007

(86) PCT No.: PCT/JP2007/064271
§ 371 (c)(1),
(2), (4) Date: Jan. 23, 2009

(87) PCT Pub. No.: WO2008/013099
PCT Pub. Date: Jan. 31, 2008

(65) Prior Publication Data
US 2010/0003630 A1  Jan. 7, 2010

(30) Foreign Application Priority Data

Jul. 25, 2006 (JP) ................. 2006-202261
Jan. 11, 2007 (JP) ................. 2007-003690
Mar. 8, 2007 (JP) ................. 2007-058592

(51) Int. Cl.
*C04B 35/48* (2006.01)
*C09K 3/00* (2006.01)
*A61C 7/12* (2006.01)
*A61C 13/08* (2006.01)

(52) U.S. Cl.
USPC ............ 428/701; 428/702; 433/8; 433/202.1; 106/35; 501/103

(58) Field of Classification Search
None
See application file for complete search history.

(56) References Cited

U.S. PATENT DOCUMENTS 4,742,030 A   5/1988  Masaki et al.
4,774,041 A * 9/1988  Tsukuma et al. ............. 264/664
(Continued)

FOREIGN PATENT DOCUMENTS

JP    60-54972 A   3/1985
JP    60-86073 A   5/1985
(Continued)

OTHER PUBLICATIONS

Ardlin, Dental Materials, 18, 2002, pp. 590-595.*
(Continued)

*Primary Examiner* — FVera Katz
(74) *Attorney, Agent, or Firm* — Westerman, Hattori, Daniels & Adrian, LLP (57) ABSTRACT

The invention relates to the use of a sintered body obtained by subjecting a primary sintered body having a relative density of 95% or higher produced from a fine yttria-containing zirconia powder to HIP sintering at a temperature of 1,200-1,600° C. and a pressure of 50 MPa or higher. This sintered body is either a sintered body which has a total light transmittance, as measured at a thickness of 0.5 mm, of 43% or higher and a three-point bending strength of 1,700 MPa or higher or a zirconia sintered body which has a total light transmittance, as measured at a thickness of 1 mm, of 40% or higher and a three-point bending strength of 500 MPa or higher and which combines high strength and total light transmission.

8 Claims, 3 Drawing Sheets

(56) References Cited

U.S. PATENT DOCUMENTS

| | | | |
|---|---|---|---|
| 4,915,625 | A | 4/1990 | Tsukuma et al. |
| 6,087,285 | A | 7/2000 | Oomichi et al. |
| 6,713,421 | B1 | 3/2004 | Hauptmann et al. |
| 2002/0031675 | A1 | 3/2002 | Cales et al. |
| 2003/0031984 | A1* | 2/2003 | Rusin et al. ............... 433/215 |
| 2004/0145070 | A1* | 7/2004 | Van der Zel ................ 264/16 |

FOREIGN PATENT DOCUMENTS

| | | |
|---|---|---|
| JP | 60-226457 A | 11/1985 |
| JP | 60-235762 A | 11/1985 |
| JP | 62-91467 A | 4/1987 |
| JP | 62-153163 A | 7/1987 |
| JP | 1-113038 A | 5/1989 |
| JP | 3-80153 A | 4/1991 |
| JP | 3-170148 A | 7/1991 |
| JP | 6-172031 A | 6/1994 |
| JP | 8-002965 A | 1/1996 |
| JP | 8-117248 A | 5/1996 |
| JP | 11-116328 A | 4/1999 |
| JP | 11-240757 A | 9/1999 |
| JP | 11-276504 A | 10/1999 |
| JP | 2000-191372 A | 7/2000 |
| JP | 2001-68754 A | 3/2001 |
| JP | 2003-506309 A | 2/2003 |
| JP | 2003-530970 A | 10/2003 |
| JP | 2006-104024 A | 4/2006 |

OTHER PUBLICATIONS

Quinn et al. Dental Materials 19, 2003 pp. 603-611.*

Kosmac. Key Engineering Materials. 254-256, 2004, pp. 683-686.*

K. Tsukuma et al., "Hot Isostatic Pressing of $Y_2O_3$-Partially Stabilized Zirconia", American Ceramic Society, Feb. 1985, pp. 310-313, vol. 64, No. 2.: Cited in Specification.

S. Somiya et al., "Zirconia Ceramics 8", Uchida Rokakuho, pp. 33-43, 1986; Cited in Specification.

International Search Report of PCT/JP2007/064271; Mailing Date of Sep. 18, 2007.

European Office Action dated Mar. 31, 2011, issued in corresponding European Patent Application No. 07791025.5.

Supplementary European Search Report dated Sep. 9, 2010, issued in corresponding European Patent Application No. 07791025.5.

Solomah, A . G.; "Sinter-Plus-Hiping of Zirconia and Zirconia-Toughened Alumina (ZTA) Ceramic Matrix Composites"; Ceramic Engineering and Science Proceedings, American Ceramic Society Inc. US, vol. 18, No. 3A , Jan. 1, 1997, pp. 219-226, XP001015802.

Japanese Office Action dated Sep. 18, 2012, issued in corresponding Japanese Patent Application No. 2007-003690, with English translation (10 pages).

Japanese Office Action dated Apr. 16, 2013, issued in corresponding Japanese Patent Application No. 2007-058592, w/ English translation.

European Office Action dated Feb. 28, 2013, issued in corresponding European Patent Application No. 07791025.5.

Japanese Office Action dated Jan. 22, 2013, issued in corresponding Japanese Patent Application No. 2007-003690, with English translation (7 pages).

Japanese Office Action dated Oct. 16, 2012, issued in corresponding Japanese Patent Application No. 2007-058592, with English translation (12 pages).

* cited by examiner

ZIRCONIA SINTERED BODIES WITH HIGH TOTAL LIGHT TRANSMISSION AND HIGH STRENGTH, USES OF THE SAME, AND PROCESS FOR PRODUCING THE SAME

TECHNICAL FIELD

The present invention relates to zirconia sintered bodies having high strength and excellent in translucency. More particularly, the invention relates to zirconia sintered bodies which are for use in dental applications and are suitable for use as a material for artificial teeth, orthodontic bracket, and mill blank for dental materials.

BACKGROUND ART

A zirconia sintered body containing a small amount of $Y_2O_3$ in solution as a stabilizer (hereinafter referred to as Y-TZP) is in extensive use as mechanical/structural materials, e.g., cutting tools, dies, nozzles, and bearings, and biomaterials such as dental materials because of the high strength and high toughness thereof. In the case of dental materials, not only mechanical properties including high strength and high toughness are required but also optical properties including translucency and color tone are required from an aesthetic standpoint.

Investigations directed only to mechanical properties, i.e., strength enhancement, of Y-TZP have hitherto been made.

The mechanism of strength enhancement in Y-TZP is based on the martensitic transition of the tetragonal-phase zirconia contained in the sintered body to a monoclinic phase by stress. In ordinary-pressure sintering, which is a general process for producing Y-TZP, large voids remain in the sintered body. The fracture strength of such a sintered body is influenced by the size of large voids, and the sintered body obtained by ordinary-pressure sintering and containing large voids remaining therein has a three-point bending strength of about 1,200 MPa. In order to forcedly eliminate such voids, investigations are being made on strength enhancement with a hot isostatic press (hereinafter abbreviated to HIP) or a hot press.

Non-patent document 1 has reported the three-point bending strength of a zirconia sintered body having an yttria concentration of 2-3 mol % produced by the HIP pressure sintering method. This sintered body has a higher strength than the sintered body obtained by ordinary-pressure sintering. However, the sintered body produced by the HIP pressure sintering method has an average strength of about 1,700 MPa at the most and has insufficient translucency.

Patent documents 1 to 3 disclose that a composite sintered body composed of zirconia having an yttria concentration of 2-4 mol % and an oxide, such as alumina, and produced by the pressure sintering method using an HIP or the like has a strength as high as 2,000 MPa or above. Zirconia having an yttria concentration of 2-4 mol % and containing no oxide such as alumina is shown therein as a Comparative Example. However, this comparative sintered body has an average strength as low as 1,650 MPa and has insufficient translucency, like the sintered body of non-patent document 1.

Patent document 4 discloses, like patent documents 1 to 3, that a composite sintered body composed of zirconia having an yttria concentration of 2-4 mol % and alumina has a strength as high as 2,000 MPa or above. As a Comparative Example zirconia having an yttria concentration of 2-4 mol % and containing no oxide such as alumina is shown therein which has an average strength of 1,854 MPa at the most.

However, this sintered body has insufficient translucency like the sintered body of non-patent document 1.

For obtaining a sintered body having both translucency and color tone, there is a method in which a black sintered body obtained with an argon HIP is oxidized by heating in the air (see non-patent document 2). However, there is a problem that the re-oxidation results in a decrease in sintered body strength.

On the other hand, orthodontic brackets made of zirconia containing yttria have been disclosed as an article having some degree of translucency (see patent documents 5 to 7). These brackets each are produced with an oxygen-containing-gas HIP and are insufficient in strength and transmittance.

Hitherto, no Y-TZP has been obtained which combines a strength as high as 1,700 MPa or above with translucency and color tone, which are required from an aesthetic standpoint. It has been impossible to obtain a sintered body having a strength of 1,900 MPa or higher from zirconia having an yttria concentration of 2-4 mol % without combining the zirconia with an oxide such as alumina used in an amount of 1 wt % or larger, practically 10 wt % or larger.

On the other hand, among zirconia sintered bodies having especially high translucency, there is single-crystal cubic zirconia for use as an artificial gem, etc. Cubic zirconia is being produced by the so-called skull melting method, which includes placing a powder of zirconium oxide in a crucible, adding 10-20% $Y_2O_3$ thereto as a stabilizer, and then melting the zirconium oxide by high-frequency heating (see, for example, patent document 8).

However, the cubic zirconia is single-crystalline and is produced through heating at a temperature of 2,000° C. or higher, which exceeds the melting point of zirconia. The translucent zirconia obtained as a sintered body must be subjected to cutting in order to impart a desired shape thereto. The skull melting method has hence been unsuitable for use as an industrial process.

With respect to a polycrystalline transparent zirconia sintered body, a process for producing the sintered body is known in which a mixture obtained by adding 8-10% or more yttria and 5-10% or more $TiO_2$ to zirconia is treated with a hot isostatic press (HIP) at a high temperature of 1,500° C. or above (see, for example, patent document 9). The patent document discloses that such a sintered body can be a transparent sintered body which has high translucency and has an in-line transmittance exceeding 40%.

However, such a zirconia sintered body to which enhanced translucency have been imparted by adding different elements has a bending strength as low as about 200 MPa and has hence been unusable in applications where high strength is required.

As a result of recent progress in the technology of precision processing using a CAD/CAM system, a process has come to be employed in which an artificial tooth is produced from a zirconia sintered body block. For example, a lowly sintered Y-TZP block is ground into a desired artificial-tooth shape by the system and then burned at a temperature of about 1,300° C. to obtain a sintered body having a high density. The sintered body thus produced has a problem that it has low translucency although high in strength. Use of this sintered body has hence been limited to molar teeth, which are not especially required to have aesthetic properties. As materials having higher translucency for use as, e.g., fore-teeth, glass ceramics are mainly used, such as leucite and lithium silicate. These glass ceramics have a contrast ratio, which is an index to translucency, as low as about 60% and have attained aesthetic properties akin to those of natural teeth from the standpoint of translucency. However, those glass ceramics have poor strength. Specifically, the glass ceramics have a bending strength as low as 100-300 MPa and a fracture toughness as low as about 1.0-3.0 MPa·m$^{0.5}$. There has been a problem that the glass ceramics, when used as a dental material, have low mechanical strength and are apt to chip or crack during use.

A zirconia sintered body for use as a dental material, such as an artificial tooth or an orthodontic bracket, must have not only high strength but also aesthetic properties based on translucency. The zirconia sintered bodies which have been reported are ones which have low strength or ones which have high strength but do not sufficiently reconcile the strength and translucency concerning an aesthetic standpoint.

Especially in applications to orthodontic brackets among dental materials, there is a desire for a sintered body having higher strength and excellent translucency.

Patent Document 1: JP-A-60-86073
Patent Document 2: JP-A-60-226457
Patent Document 3: JP-A-60-235762
Patent Document 4: JP-A-3-80153
Patent Document 5: JP-A-3-170148
Patent Document 6: JP-A-08-117248
Patent Document 7: JP-A-11-276504
Patent Document 8: JP-A-06-172031
Patent Document 9: JP-A-62-91467
Non-Patent Document 1: *Ceramics Bulletin*, Vol. 64, p. 310 (1985)
Non-Patent Document 2: Shigeyuki Somiya and Masahiro Yoshimura e.d., *Zirconia Ceramics* 8, Uchida Rokakuho, pp. 33-43 (1986)

DISCLOSURE OF THE INVENTION

Problems that the Invention is to Solve

An object of the invention is to provide zirconia sintered bodies having high strength and aesthetic properties based on translucency.

Means for Solving the Problems

The present inventors diligently made investigations in order to obtain a Y-TZP sintered body which combines high strength, translucency, and color tone. As a result, they have found that a sintered body satisfying both of translucency and strength can be obtained by using an improved HIP method as a technique for improving strength. In particular, it has been found that whether a sintered body satisfying both of translucency and strength can be obtained or not depends considerably on the structure, in particular, crystal grain size, of a primary sintered body to be subjected to an HIP treatment. They have found that a high strength which has not been obtained and high translucency can be attained substantially with Y-TZP only, without the necessity of combining with a large amount, i.e., 1 wt % or more, of other element(s). The object of the invention is accomplished with the following constitutions.

(1) A high-strength yttria-containing zirconia sintered body which comprises zirconia containing 2-4 mol % yttria and has a three-point bending strength of 1,700 MPa or higher and a total light transmittance, as measured at a thickness of 0.5 mm, of 43% or higher.

(2) The zirconia sintered body according to (1) which has a three-point bending strength of 1,900 MPa or higher and a total light transmittance, as measured at a thickness of 0.5 mm, of 45% or higher.

(3) The zirconia sintered body according to any one of (1) and (2) characterized by being made of crystal phases which are constituted only of a fluorite type tetragonal crystal phase (I) containing 3 mol % or less yttria or constituted of a mixed phase comprising a fluorite type tetragonal crystal phase (I) containing 3 mol % or less yttria and a fluorite type tetragonal crystal phase (II) containing 5 mol % or more yttria, the proportion of the fluorite type tetragonal crystal phase (I) being 50-100%.

(4) The zirconia sintered body according to any one of (1) to (3) characterized by containing no voids of 10 μm or larger and having a porosity of 0.5% or lower.

(5) A translucent yttria-containing zirconia sintered body which comprises zirconia containing yttria in an amount larger than 4 mol % and not larger than 6 mol % and has a grain size of 2.0 μm or smaller, a relative density of 99.5% or higher, and a total light transmittance, as measured at a thickness of 1 mm with visible light having a wavelength of 600 nm, of 40% or higher.

(6) The translucent yttria-containing zirconia sintered body according to (5) which has a contrast ratio, as measured at a thickness of 1 mm with light having a wavelength of 600 nm, of 60% or lower.

(7) The translucent yttria-containing zirconia sintered body according to any one of (5) and (6) which has an absorbing/scattering coefficient, as measured with visible light having a wavelength of 600 nm, of 4.0 mm$^{-1}$ or lower.

(8) The translucent yttria-containing zirconia sintered body according to any one of (5) to (7) which has a three-point bending strength of 500 MPa or higher.

(9) The translucent yttria-containing zirconia sintered body according to any one of (5) to (8) which has a fracture toughness of 3.5 MPa·m$^{0.5}$ or higher.

(10) The translucent yttria-containing zirconia sintered body according to any one of (5) to (9) which is made of crystal phases which are constituted of a fluorite type tetragonal crystal phase and a fluorite type cubic crystal phase, the proportion of the fluorite type tetragonal crystal phase being 30%-80%.

(11) A dental material comprising the zirconia sintered body according to any one of (1) to (10).

(12) An orthodontic bracket comprising the zirconia sintered body according to any one of (1) to (10).

(13) An artificial tooth comprising the zirconia sintered body according to any one of (1) to (10).

(14) A mill blank for dental materials which comprises the zirconia sintered body according to any one of (1) to (10).

(15) A process for producing a zirconia sintered body which comprises subjecting a primary sintered body obtained by molding an yttria-containing zirconia powder and sintering the molding without pressurization to a treatment with a hot isostatic press (HIP) at a high temperature and a high pressure, characterized in that the primary sintered body to be used has a relative density of 95% or higher and is treated at a temperature of 1,200-1,600° C. and a pressure of 50 MPa or higher.

(16) The process according to (15) characterized in that the primary sintered body has a grain size of 0.3 μm or smaller.

(17) The process according to any one of (15) and (16) characterized in that the yttria-containing zirconia powder has a purity of 99% or higher, a specific surface area of 5-20 m$^2$/g, and a crystallite size of 10-70 nm.

(18) The process according to any one of (15) to (17) wherein the yttria-containing zirconia powder contains at least one of the following alumina compounds as a sintering aid in a total amount of 1 wt % or smaller:

alumina compounds: alumina ($Al_2O_3$), spinel ($MgO.Al_2O_3$), YAG ($5Al_2O_3.3Y_2O_3$), mullite ($3Al_2O_3 \cdot 2SiO_2$), and aluminum borate compounds ($nB_2O_3 \cdot Al_2O_3$; n=0.5, 1, or 2).

(19) The process according to any one of (15) to (18) characterized in that a semi-sealed vessel is disposed in an HIP treatment apparatus and the sintered body obtained without pressurization is disposed in the vessel and treated.

(20) The process according to any one of (15) to (19) characterized in that a semi-sealed vessel constituted of a ceramic vessel having an opening and a ceramic flat plate placed over the opening is disposed in an HIP treatment apparatus and the sintered body obtained without pressurization is disposed in the vessel and treated.

Advantages Of The Invention

The sintered bodies of the invention have not only high strength but also aesthetic properties based on translucency. The sintered bodies are hence applicable, of course, to mechanical/structural materials such as cutting tools, dies, nozzles, bearings, and rollers, and are especially effective as a material for artificial teeth or an orthodontic bracket which are utilized in the dental field.

BEST MODE FOR CARRYING OUT THE INVENTION

The invention is explained below in detail.

The sintered bodies of the invention are: a high-strength yttria-containing zirconia sintered body which is made of zirconia containing yttria as a stabilizer in an amount of from 2 mol % to 4 mol % and has an average three-point bending strength of 1,700 MPa or higher and a total light transmittance, as measured at a thickness of 0.5 mm, of 43% or higher, in particular, the high-strength yttria-containing zirconia sintered body which has an average three-point bending strength of 1,900 MPa or higher and a total light transmittance, as measured at a thickness of 0.5 mm, of 45% or higher; and a translucent yttria-containing zirconia sintered body which is a zirconia sintered body containing yttria as a stabilizer in an amount larger than 4 mol % and not larger than 6 mol % and which has a grain size of 2.0 µm or smaller, a relative density of 99.5% or higher, and a total light transmittance, as measured at a thickness of 1 mm with visible light having a wavelength of 600 nm, of 40% or higher. The invention further relates to uses of these sintered bodies as dental materials and to a process for producing the sintered bodies.

First, an explanation is given on the high-strength yttria-containing zirconia sintered body which contains yttria as a stabilizer in an amount of from 2 mol % to 4 mol % and has an average three-point bending strength of 1,700 MPa or higher and a total light transmittance, as measured at a thickness of 0.5 mm, of 43% or higher, in particular, the especially high-strength yttria-containing zirconia sintered body which has an average three-point bending strength of 1,900 MPa or higher and a total light transmittance, as measured at a thickness of 0.5 mm, of 45% or higher (hereinafter referred to as "high-strength sintered body").

In case where the concentration of the stabilizer is lower than 2 mol %, not only a reduced strength results but also the crystal phases are instable, making it difficult to produce the sintered body. On the other hand, concentrations thereof exceeding 4 mol % tend to result in a reduced strength. Yttria concentrations suitable for high strength are in the range of 2-4 mol %, in particular, 2.5-3 mol %, while yttria concentrations suitable for total light transmittance are in the range of 3-4 mol %. A maximum strength is reached at around 3 mol %, while total light transmittance tends to become higher as yttria concentration increases.

The high-strength sintered body of the invention has an especially high strength, and the average three-point bending strength thereof is 1,700 MPa or higher, preferably 1,900 MPa or higher, especially preferably 2,000 MPa or higher. Under optimal conditions, the average three-point bending strength of the sintered body is as high as 2,100 MPa.

The high-strength sintered body of the invention has excellent translucency. The total light transmittance thereof, as measured at a thickness of 0.5 mm, is 43% or higher, especially 45% or higher. It is preferred that the total light transmittance thereof should be especially 48% or higher, more preferably about 50%.

Those values of strength and translucency are not attainable by any sintered body obtained by the conventional HIP method.

The intrinsic color tone of zirconia is white, and zirconia is ivory-white when it contains an impurity such as, e.g., iron or nickel, in an amount of tens of ppm.

It is more preferred that the high-strength sintered body of the invention should be made of crystal phases which are constituted only of a fluorite type tetragonal crystal phase (I) containing 3 mol % or less yttria or constituted of a mixed phase including a fluorite type tetragonal crystal phase (I) containing 3 mol % or less yttria and a fluorite type tetragonal crystal phase (II) containing 5 mol % or more yttria, the proportion of the fluorite type tetragonal crystal phase (I) being 50-100%. The mechanism of strength enhancement in zirconia is based on the transition of a fluorite type tetragonal crystal phase (I) to a monoclinic phase by stress application. Because of this, the presence of a fluorite type tetragonal crystal phase (I) is essential for strength enhancement.

The high-strength sintered body of the invention preferably contains no voids of 10 µm or larger therein. In particular, it is preferred that the sintered body should have a porosity of 0.5% or lower. Since the strength and translucency of a sintered body are influenced by the amount and size of the voids present therein, a sintered body having high strength and high translucency satisfies those requirements. The high-strength sintered body of the invention is one in which the amount and size of voids have been reduced to realize improvements in strength and translucency.

Next, an explanation is given on the zirconia sintered body having an especially high total light transmittance (hereinafter referred to as "highly translucent sintered body") which contains yttria as a stabilizer in an amount larger than 4 mol % and not larger than 6 mol % and has a grain size of 2.0 µm or smaller, a relative density of 99.5% or higher, and a total light transmittance, as measured at a thickness of 1 mm with visible light having a wavelength of 600 nm, of 40% or higher.

The content of $Y_2O_3$ in the highly translucent sintered body of the invention is higher than 4 mol % and not higher than 6 mol %.

It is generally said that for imparting translucency, it is important to increase the size of crystal grains and thereby reduce the number of grain boundaries per unit thickness in order to reduce the optical anisotropy of crystals. When the $Y_2O_3$ content in the zirconia sintered body is 4 mol % or lower, this sintered body has an increased strength. However, such too low $Y_2O_3$ contents tend to result in a crystalline structure constituted mainly of tetragonal crystals and in a decrease in translucency because of light scattering due to the crystalline structure. On the other hand, in case where the $Y_2O_3$ content therein exceeds 6 mol %, this sintered body has a reduced strength although high in in-line light transmittance.

When the $Y_2O_3$ content therein is higher than 4 mol % and not higher than 6 mol %, the crystal systems of the sintered body are a mixture of a tetragonal crystalline structure and a cubic crystalline structure. There are cases where boundaries between different crystal systems reduce translucency based on an increase in refractive index. However, the sintered body of the invention can be a zirconia sintered body combining translucency and strength because this sintered body has the $Y_2O_3$ content according to the invention and is constituted of fine grains of 2 μm or smaller.

The highly translucent sintered body of the invention has a sintered body grain size of 2 μm or smaller. It is preferred that the grain size thereof should be especially 1 μm or smaller, more preferably 0.6 μm or smaller. In case where the crystal grain size thereof exceeds 2 μm, the proportion of the tetragonal crystal phase is too small, resulting in a large decrease in strength. In addition, the light absorbing/scattering coefficient increases due to light scattering at grain boundaries, resulting in a decrease in in-line transmittance. Although the lower limit of the crystal grain size is not particularly limited, it is preferably 0.4 μm or larger.

The density of the highly translucent sintered body of the invention is 99.5% or higher, especially preferably 99.9% or higher, in terms of relative density. In case where the relative density thereof is lower than 99.5%, this sintered body has a contrast ratio, as measured at a wavelength of 600 nm, exceeding 60% due to light scattering by voids present in the sintered body. Consequently, high translucency cannot be attained.

The highly translucent sintered body of the invention has a total light transmittance, as measured at a thickness of 1 mm with visible light having a wavelength of 600 nm, of 40% or higher. In case where the total light transmittance thereof is lower than 40%, this sintered body has insufficient aesthetic properties.

In case where the content of $Y_2O_3$ therein is lower than the lower limit of the range according to the invention, this sintered body has a reduced total light transmittance. The highly translucent sintered body of the invention has a total light transmittance of 40% or higher even when it has a thickness of 1 mm. That transmittance value corresponds to a total light transmittance of at least 45% for the sintered body having a thickness of 0.5 mm.

It is preferred that the highly translucent sintered body of the invention should have a contrast ratio, as measured at a thickness of 1 mm with light having a wavelength of 600 nm, of 60% or lower, and that the sintered body should further have an absorbing/scattering coefficient, as measured with 600-nm visible light, of 4.0 $mm^{-1}$ or lower. In case where a sintered body has a high contrast ratio and a high absorbing/scattering coefficient, this sintered body not only has low translucency but causes light refraction and scattering. Such a sintered body hence has a problem that when used as an artificial tooth or orthodontic bracket, the sintered body attached or worn is conspicuous. Smaller values of those properties are preferred.

The highly translucent sintered body of the invention preferably has a strength, in terms of three-point bending strength, of 500 MPa or higher, especially 900 MPa or higher, more preferably 1,000 MPa or higher. In case where the strength thereof is too low, processing of the sintered body or use thereof as a dental material may encounter a problem concerning cracking.

Furthermore, the highly translucent sintered body preferably has a fracture toughness of 3.5 $MPa \cdot m^{0.5}$ or higher. Especially in dental material applications such as artificial teeth and orthodontic brackets, not only bending strength but also fracture toughness are important. The fracture toughness thereof is especially preferably 4.0 $MPa \cdot m^{0.5}$ or higher.

For the highly translucent sintered body of the invention, a balance between bending strength and total light transmittance is important. Bending strength and total light transmittance tend to be inconsistent with each other. This sintered body of the invention, however, can combine a total light transmittance, as measured at a thickness of 1 mm, of 40-42% or higher and a three-point bending strength of 1,000-1,200 MPa or higher.

It is preferred that the highly translucent sintered body of the invention should be made of crystal phases which are constituted of a fluorite type tetragonal crystal phase and a fluorite type cubic crystal phase, and in which the proportion of the fluorite type tetragonal crystal phase is 30%-80%. In case where the proportion of the fluorite type tetragonal crystal phase is lower than 30%, fracture toughness decreases and, hence, high strength cannot be obtained. On the other hand, in case where the proportion of the fluorite type tetragonal crystal phase exceeds 80%, boundary scattering due to crystal anisotropy is enhanced, resulting in reduced translucency.

A process for producing the sintered bodies of the invention is explained below.

The sintered bodies of the invention can be produced by a process which includes subjecting a primary sintered body obtained by molding an yttria-containing zirconia powder and sintering the molding without pressurization to a treatment with a hot isostatic press (HIP) at a high temperature and a high pressure, wherein the primary sintered body to be used has a relative density of 95% or higher and the HIP treatment is conducted at a temperature of 1,200-1,600° C. and a pressure of 50 MPa or higher.

In the process including molding an yttria-containing zirconia powder, sintering the molding without pressurization, and then treating the resultant primary sintered body with a hot isostatic press (HIP) at a high temperature and a high pressure, it is especially preferred that the primary sintered body should be one which has a grain size of 0.3 μm or smaller and a relative density of 95% or higher.

The powder molding may be conducted by a method in common use for ceramics. For example, all of techniques such as press molding, cold isostatic press (CIP) molding, casting, extrusion molding, and injection molding can be applied.

The HIP treatment is conducted for the purpose of eliminating residual voids present in the sintered body. Although temperatures of 1,200-1,600° C. are usable, it is preferred to use a temperature of 1,400° C. or higher from the standpoint of reconciling high strength and high translucency.

As a pressure medium for the HIP, argon gas in common use suffices. Although a pressure of 50 MPa or higher is necessary, a sufficient effect is obtained at a pressure of 100-200 MPa, which is in common use.

The primary sintered body to be used in the invention has a relative density of 95% or higher. In case where the relative density thereof is lower than 95%, argon gas infiltrates into inner parts of the sintered body to reduce translucency.

In the invention, it is preferred that the sintered body to be obtained without pressurization and subjected to the HIP treatment should be regulated so as to have a grain size of 0.3 µm or smaller. This regulation makes it possible to attain an especially high strength of 1,900 MPa or above. For obtaining a sintered body having a grain size as small as 0.3 µm or below and densified to 95% or higher, it is preferred to use a powder having excellent suitability for low-temperature sintering.

By regulating the primary sintered body to be subjected to the HIP treatment so as to have an average crystal grain size of 0.3 µm or smaller and to have been densified to a relative density of 95% or higher, the high-pressure-gas infiltration into inner parts of a sintered body having a relative density lower than 95% in an HIP treatment can be prevented. The average grain size of the sintered body is preferably 0.3 µm or smaller, more preferably 0.25 µm or smaller.

The smaller the average crystal grain size of the sintered body to be subjected to the HIP treatment, the more the strength of the HIP-treated sintered body improves. It is thought that the smaller the grain size of a primary sintered body, the more the plastic flow of grains under high pressure in an HIP is enhanced and the more the elimination of residual voids is accelerated. The average crystal grain size of a sintered body depends on sintering temperature. For example, 0.3 µm and 0.25 µm are obtained with about 1,300° C. and about 1,250° C., respectively.

Suitable raw-material powders are ones each composed of fine grains having a purity of 99% or higher, specific surface area of 5-20 m$^2$/g, and crystallite size of 10-70 nm. Suitable powders which, through sintering at 1,300° C. or lower, give a sintered body densified to 95% or higher are ones having a large specific surface area. Especially suitable are ones having a specific surface area of 15-20 m$^2$/g.

Even when alumina ($Al_2O_3$), spinel ($MgO.Al_2O_3$), YAG ($5Al_2O_3.3Y_2O_3$), mullite ($3Al_2O_3.2SiO_2$), an aluminum borate compound ($nB_2O_3.Al_2O_3$; n=0.5, 1, or 2) or the like is used as an aid for the purpose of lowering a sintering temperature, the transparency which is a target property in the invention can be obtained. The amount of those ingredients is regulated to 1 wt % or smaller in order to satisfy the properties according to the invention.

For obtaining a sintered body densified to 95% or higher through sintering conducted at a temperature as low as possible, a suitable raw-material powder is a powder obtained by adding up to 1 wt % sintering aid to a powder composed of fine grains having a purity of 99% or higher, specific surface area of 5-20 m$^2$/g, and crystallite size of 10-70 nm. The amount of the sintering aid to be added is preferably 0.5 wt % or smaller, optimally 0.1-0.3 wt %. This is because excessive addition elevates rather than lowers the sintering temperature.

Powders containing 0.25 wt % alumina are on the market (e.g., zirconia powder 3YE, manufactured by Tosoh Corp.). However, the present inventors found out sintering aids equal or superior to alumina in aid effect. Such sintering aids are spinel, YAG, mullite, and aluminum borate oxides, all of which are alumina composite oxides. In particular, spinel addition gives a sintered body having a smaller grain size than alumina addition through sintering at the same temperature. For example, the 1,300° C. sintering of a powder containing 0.25 wt % alumina results in a grain size of 0.3 µm, while that of a powder containing 0.35 wt % spinel results in an even smaller grain size of 0.25 µm. The addition of such a sintering aid in a slight amount makes it possible to conduct sintering at a low temperature of 1,200-1,250° C., and a sintered body is obtained which has a crystal grain size as small as 0.15 µm to 0.2 µm and a relative density of 95% or higher.

In the production process according to the invention, an HIP treatment is conducted using a non-oxidizing gas, e.g., argon gas, as a pressure medium. It is especially preferred that a semi-sealed vessel should be disposed in the HIP treatment apparatus and the sintered body obtained without pressurization be disposed in this vessel and treated. By conducting such a semi-sealed HIP treatment, an especially high total light transmittance can be obtained.

The vessel to be used may be, for example, one made of an oxide ceramic such as alumina or zirconia. The term "semi-sealed" as used in the invention means not a completely closed atmosphere but a state in which the movement of the medium gas as a pressure medium is inhibited inside and outside the ceramic vessel during the HIP treatment. In such a state, the atmosphere of the medium gas in the HIP treatment apparatus differs from the atmosphere of the medium gas around the sintered body obtained without pressurization and placed in the ceramic vessel.

The semi-sealed state in the invention does not require a high degree of airtightness, and is a sealed state in a degree which is attained, for example, by placing a flat alumina plate over the opening of an alumina crucible or burning pot. In case where the primary sintered body is subjected to an HIP treatment in a vessel not in a semi-sealed state, this sintered body blackens. However, sintering in a semi-sealed vessel as in the invention does not color the sintered body. Although the blackened sintered body can be caused to recover the original color by annealing the sintered body by reheating it at 800° C. or higher in an oxidizing atmosphere, this annealing reduces the strength of the sintered body. In addition, a high total light transmission on the level attainable by the invention is not obtained.

The reason why a sintered body having an especially high total light transmittance, having high strength and having no coloration is obtained by the process of the invention has not been fully elucidated. However, it is thought that when the treatment is conducted in a vessel which is not in a semi-sealed state, then a slight amount of a carbon ingredient comes into the sintered body and this ingredient gasifies upon re-heating to form microvoids, which impair translucency and strength. The carbon ingredient is thought to consist mainly of the carbon monoxide gas generated by the reaction of the oxygen remaining in a slight amount in the argon gas medium with the carbon used in the heating element or heat-insulating material employed in the HIP apparatus. In the invention, the sintered body is disposed in a semi-sealed space and this is thought to reduce the frequency of contact between the sintered body and the carbon monoxide gas to inhibit the carbon ingredient from coming into the sintered body.

Uses of the sintered bodies of the invention are explained next.

A technique for producing an artificial zirconia tooth with a CAD-CAM system was recently developed and has been put to practical use. In this production technique, the skeleton shape of an artificial tooth is incorporated into a CAD unit and information thereon is transferred to a milling (CAM) unit to automatically process a mill blank made of zirconia and complete a precise shape. Known typical systems include: a system in which a powder calcine which has not been sintered is used as a mill blank and processed into a size allowing for sintering shrinkage, and this processed blank is sintered; and a system in which a sintered body itself is used as a mill blank and processed. Examples of the former system include Cercon and Lava, while examples of the latter system include DC-Zircon.

A zirconia sintered body to be used as an artificial tooth is required to have strength and translucency. Hitherto, sintered bodies obtained by the ordinary-pressure sintering of zirconia containing 3 mol % $Y_2O_3$ have been used, and some of these have a strength of 1,000-1,400 MPa. However, all these sintered bodies have a total light transmittance, as measured at a thickness of 0.5 mm, of 30-40% at the most. There have also been sintered bodies treated with an HIP for the purpose of improving strength and translucency. However, as stated above, the sintered bodies obtained through ordinary HIP treatments have a total light transmittance of about 40% at the most although they have attained a strength of 1,600-1,850 MPa.

The HIP-treated sintered bodies of the invention are a high-strength sintered body having a total light transmittance, as measured at a thickness of 0.5 mm, of 43% or higher and a strength of 1,700 MPa or higher and a highly translucent sintered body having a total light transmittance, as measured at a larger thickness of 1 mm, of 40% or higher. These sintered bodies each can be a material for artificial teeth which is superior to conventional sintered bodies in reliability and aesthetic properties. This effect is presumed to be produced because voids of 10 μm or larger have been completely eliminated and, hence, strength and total light transmittance, which are properties governed by voids, are improved.

Figure 3:
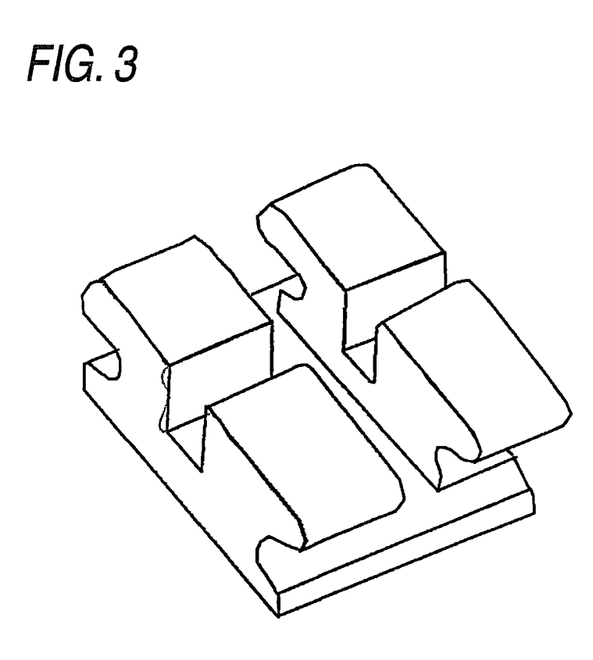
FIG. 3 is a view showing an example of appearances of an orthodontic bracket.

The sintered bodies of the invention are suitable for use also as the main body of an orthodontic bracket and as parts for the bracket. In recent years, orthodontic brackets are coming to have more complicated shapes and are hence required to have a higher material strength than before while retaining high aesthetic translucency. In FIG. 3 is shown an example of the shapes of such brackets. The sintered bodies of the invention can be effectively used as a bracket main body and peripheral parts.

For forming such a part having a complicated shape, injection molding is especially suitable. A raw-material powder is kneaded together with a thermoplastic organic resin. The resultant compound is injected into a heated mold to impart a desired shape to the compound. The resultant shape is heated in a degreasing oven to burn off the resin.

The invention will be explained below in detail by reference to Examples. However, the invention should not be construed as being limited to the following Examples.

Methods for evaluating sintered body properties in the invention are described below.

(Three-Point Bending Strength)

Three-point bending strength was measured with universal tester Autograph DCS-2000 (manufactured by Shimadzu Corp.) in accordance with JIS-R-1601. A specimen having a width of 4 mm, thickness of 3 mm, and length of 40 mm was examined under the conditions of a span of 30 mm and a crosshead speed of 0.5 mm/min. With respect to each sample, five test pieces were produced and subjected to the bending test.

(Total Light Transmittance)

Total light transmittance at a thickness of 0.5 mm was measured with turbidimeter NDH 2000 (manufactured by NIPPON DENSOKU) by the method in accordance with JIS K361-1. In this apparatus, standard light D65 is caused to strike on a sample and the light beam which has passed through the sample is detected with an integrating sphere. As the sample was used a sintered body which had a diameter of 25 mm and a thickness of 0.5 mm and each side of which had been mirror-polished.

The total light transmittance of a sintered body having a larger thickness of 1 mm was measured with a spectrophotometer (V-650) manufactured by Japan Spectroscopic Co., Ltd. A disk-form sample was used which had a thickness of 1 mm and each side of which had been mirror-polished. Visible light which had passed through the sample was collected with an integrating sphere to determine the intensity of the visible light (I). On the other hand, the intensity of visible light ($I_0$) was measured without placing the sample. The total light transmittance was calculated in terms of the proportion of the former to the latter intensity ($=I/I_0$).

Incidentally, a zirconia sintered body obtained from a zirconia powder having an yttria concentration of 3 mol % (TZ-3YE, manufactured by Tosoh Corp.) by the process of the invention (primary burning, 1,300° C.; HIP, 150 MPa×1, 500° C.) had a total light transmittance, as measured at a thickness of 0.5 mm, of 45.4% and a total light transmittance, as measured at a thickness of 1 mm with 600-nm light, of 37.2%. A relationship between the total light transmittance at 0.5-mm thickness and that at 1-mm thickness is represented by the following equation.

$$D_{0.5\,mm} = 1.214 \times D_{1\,mm,\,600\,nm}$$

$D_{0.5\,mm}$: total light transmittance at 0.5-mm thickness
$D_{1\,mm,\,600\,nm}$: total light transmittance at 1.0-mm thickness with 600-nm light (Contrast Ratio)

Contrast ratio was measured with color analyzer TC-1800MK-II, manufactured by Tokyo Denshoku, by a method including irradiating a sample with visible light and measuring the resultant reflectance. The sample used was a disk-form sample which had a thickness of 1 mm and each side of which had been mirror-polished. Visible light having a wavelength of 600 nm was caused to strike on the sample. A black plate having a visible-light reflectance of 0% was placed on the back of the sample, and the spectral reflectance of this sample (R1) was measured. Furthermore, a common standard white plate was placed on the back of the sample, and the spectral reflectance of this sample (R2) was measured. The contrast ratio was calculated in terms of proportion between these (R1/R2).

(Absorbing/Scattering Coefficient)

Absorbing/scattering coefficient (α) was determined by measuring in-line transmittance with double-beam spectrophotometer Type 220, manufactured by Hitachi Ltd., and calculating the coefficient from the value of in-line transmittance at a wavelength of 600 nm using the following equation.

$$\alpha \cdot t = -\ln(T/(1-R)^2)$$

α: absorbing/scattering coefficient ($mm^{-1}$)
t: sample thickness (mm)
T: in-line transmittance
R: reflectance (0.140 was substituted as a value at wavelength of 600 nm)

(Identification of Crystal Phases)

Crystal phases of a sintered body were identified by the Rietveld analysis after an XRD examination. In the XRD examination, X-ray powder diffractometer MAC Science MXP3 (manufactured by MAC Science) was used to examine a burned surface of the sintered body under the conditions of a 2θ range of 20-90°, step width of 0.04°, and examination period in each step of 20 seconds. In the Rietveld analysis, program Rietan-2000 was used to determine the crystal phases of each sintered body, contents thereof, and lattice constants thereof. Details of this examination and analysis are given in I. Yamashita, K. Tsukuma, *J. Ceram. Soc. Jpn.*, Vol. 113 [8] 530-533 (2005). Furthermore, the $Y_2O_3$ concentration in the tetragonal crystals was determined using equation (1) and equation (2) from the lattice constants obtained. The yttria concentration in the tetragonal crystals was determined by conversion from the lattice constants using the following equation (1). This equation is described in I. R. Gibson et al., *J. Am. Ceram. Soc.*, Vol. 84 [3] 615-618 (2001).

$$YO_{1.5} = (1.0223 - c_f/a_f)/0.001319 \quad (1)$$

$a_f$, $c_f$: lattice constants of tetragonal crystal in fluorite type structure
$YO_{1.5}$: yttria concentration
Incidentally, the $Y_2O_3$ concentration was determined by conversion using equation (2).

$$Y_2O_3 = 100 \times YO_{1.5}/(200 - YO_{1.5}) \quad (2)$$

(Average Grain Size of Sintered Body)

A sintered body was mirror-polished and thermally etched for 1 hour at a temperature lower by 50° C. than the maximum temperature which had been experienced by the sintered body. The etched surface was examined with an SEM to determine the average grain size. The SEM examination was made with scanning electron microscope JSM-5400 (manufactured by JEOL). The size was calculated using equation (3) by the method described in *J. Am. Ceram. Soc.*, 52[8] 443-446 (1969).

$$D = 1.56 L \quad (3)$$

D: average crystal grain size
L: average length of grains crossed by arbitrary straight line (Relative Density)

The density of a sintered body was determined through an underwater weight measurement conducted by the Archimedes method. The relative density was calculated using the following equation, in which the theoretical density was taken as 6.107 g/cm³ for 2 mol % $Y_2O_3$, 6.089 g/cm³ for 3 mol % $Y_2O_3$, and 6.068 g/cm³ for 4 mol % $Y_2O_3$.

$$\text{Relative density (\%)} = 100 \times (\text{density of sintered body})/(\text{theoretical density}) \quad (4)$$

(Porosity of Sintered Body)

The porosity of a sintered body was calculated using the following equation.

$$\text{Porosity of sintered body (\%)} = 100 - (\text{relative density}) \quad (5)$$

EXAMPLES 1 TO 3

(Raw-Material Powder)

A zirconia powder containing 3 mol % yttria (trade name, TZ-3YE) manufactured by Tosoh Corp. was used. This powder has a specific surface area of 15.5 m²/g and a crystallite size of 23 nm. The powder contained 0.25 wt % alumina, and the total amount of impurities, i.e., substances other than Y, Zr, O, and Al, therein was 1 wt % or smaller.

(Sample Production)

A uniaxial press and a mold were used to apply a pressure of 70 MPa to the raw-material powder to obtain platy moldings each having dimensions of 40 mm×50 mm and a thickness of 5 mm. These moldings each were put in a rubber mold and pressed with a cold isostatic press at a pressure of 200 MPa to consolidate the moldings. The consolidated moldings were sintered in the air at temperatures in the range of 1,250-1,300° C. for 2 hours to obtain primary sintered bodies. The primary sintered bodies were put in a vessel made of alumina, and a flat plate lid made of alumina was placed over the opening of the vessel to bring the inside of the vessel into a semi-sealed state. This alumina vessel was disposed in an HIP apparatus, and the primary sintered bodies were treated in an argon gas medium at temperatures of 1,400-1,500° C. and a pressure of 150 MPa. The sintered bodies thus obtained were not blackish and retained almost the same color tone as that before the treatment. The sintered bodies were subjected to the measurements of density, average grain size, and strength, determination of total light transmittance at a thickness of 0.5 mm, and examination for breakage sources.

(Results of the Measurements)

The results of the measurements of the densities of the primary sintered bodies and HIP-treated sintered bodies and the results of the measurements of bending strength and total light transmittance at 0.5-mm thickness are shown in Table 1. Incidentally, the density of 6.08 g/cm³ corresponds to a porosity of 0.15%.

TABLE 1

| | Primary Sintered Body | | | | HIP Sintered Body | | | | |
|---|---|---|---|---|---|---|---|---|---|
| Sample No. | Primary-sintering temperature ° C. | Density g/cm³ | Relative density % | Grain size μm | HIP temperature ° C. | Density$_{HIP}$ g/cm³ | Grain size$_{HIP}$ μm | Average bending strength MPa | Total light transmittance % |
| A1 | 1250 | 5.83 | 95.9 | 0.25 | 1500 | 6.08 | 0.6 | 2091 | 49 |
| A2 | 1300 | 5.99 | 98.5 | 0.30 | 1400 | 6.08 | 0.49 | 1917 | 48 |
| A3 | 1250 | 5.83 | 95.9 | 0.25 | 1400 | 6.08 | 0.49 | 1923 | 48 |

Sintered bodies shown in Table 1 were subjected to phase identification by XRD examination. The crystal structures of the sintered bodies are shown in Table 2.

TABLE 2

| Sample No. | Crystal phase | wt % | a (Å) | c (Å) | $c_f/a_f$ | $Y_2O_3$ (mol %) |
|---|---|---|---|---|---|---|
| A1 | tetragonal crystal (I) | 76.6 | 3.6042 | 5.1796 | 1.0162 | 2.37 |
| | tetragonal crystal (II) | 23.4 | 3.6248 | 5.1520 | 1.0050 | 7.01 |
| A2 | tetragonal crystal (I) | 86.4 | 3.6061 | 5.1783 | 1.0154 | 2.69 |
| | tetragonal crystal (II) | 13.6 | 3.6226 | 5.1505 | 1.0053 | 6.87 |

EXAMPLES 4 AND 5

COMPARATIVE EXAMPLE 1

Sintered bodies were produced from the raw-material powder described in Example 1 by the same sample production method as in Example 1, except that the primary sintering was conducted at temperatures of 1,400-1,600° C. and the HIP treatment was conducted at temperatures of 1,250-1,400° C. The densities of the primary sintered bodies and HIP-treated sintered bodies and the bending strengths and total light transmittances at 0.5-mm thickness of the sintered bodies are shown in Table 3.

When a sintering temperature of 1,600° C. was used to produce a primary sintered body, this primary sintered body had an average grain size as large as 1.45 μm. The HIP-treated sample obtained had a strength as low as 1,058 MPa and was low also in total light transmittance at 0.5-mm thickness.

Figure 1A:
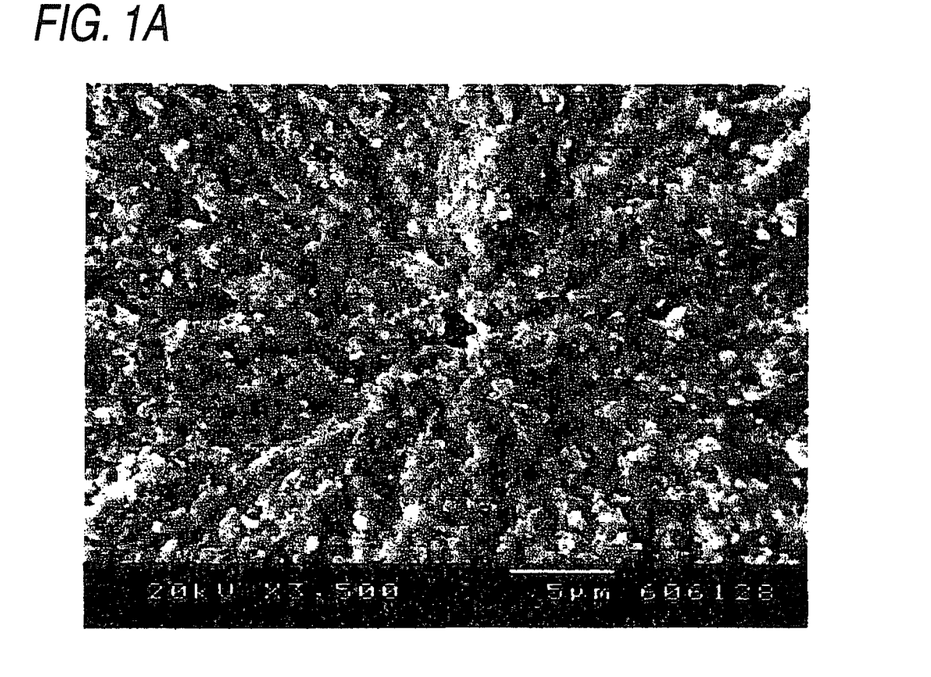
FIG. 1A is a view showing breakage sources in a high-strength sintered body (Sample No. A1 in Table 1) according to the invention.
Figure 1B:
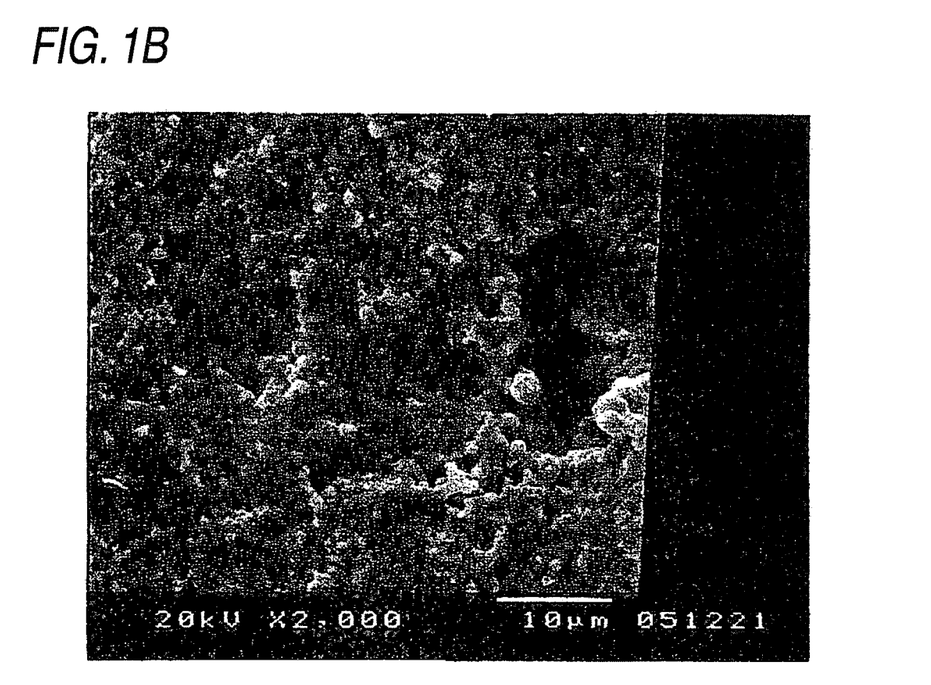
FIG. 1B is a view showing breakage sources in the sintered body of Comparative Example 2 (Sample No. B2 in Table 3).

The sintered bodies of Example 1 (A1 in Table 1) and Comparative Example 1 (B2 in Table 3) were examined with an SEM for breakage sources, and the results thereof are shown in FIG. 1A and FIG. 1B. The breakage sources in Example 1 each were a void having a size of smaller than 10 μm, whereas those in Comparative Example 1 included voids of 10 μm or larger.

COMPARATIVE EXAMPLE 2

A primary sintered body produced in the same manner as in Sample No. A1 in Example 1 was put in a vessel made of graphite. This vessel was disposed in an HIP apparatus without covering the opening of the vessel, and the primary sintered body was treated in an argon gas medium at a temperature of 1,500° C. and a pressure of 150 MPa. The sintered body thus obtained was blackish. This sintered body was oxidized in the air at 1,200° C. for 2 hours to return the color thereof to almost the same color as before the HIP treatment. This sample had an average bending strength of 1,250 MPa and a total light transmittance of 35%. This sample was lower in both strength and total light transmittance than the sample of Example 1.

EXAMPLES 6 TO 47

(Sintering-Aid-Containing Powders)

To a zirconia powder containing 3 mol % yttria (trade name, TZ-3Y) manufactured by Tosoh Corp. was added alumina, spinel, YAG, mullite, or an aluminum borate compound in an amount of 0.31 mol % in terms of $Al_2O_3$ amount. The ingredients were mixed together by means of a ball mill. Thus, raw-material powders were obtained. With respect to the aluminum borate compound, alumina ($Al_2O_3$) and boric acid ($B_2O_3$) were added to the zirconia powder to obtain raw-material powders.

TABLE 3

| | Primary Sintered Body | | | HIP Sintered Body | | | | |
|---|---|---|---|---|---|---|---|---|
| Sample No. | Primary-sintering temperature ° C. | Density g/cm³ | Relative density % | Grain size μm | HIP temperature ° C. | Density$_{HIP}$ g/cm³ | Grain size$_{HIP}$ μm | Average bending strength MPa | Total light transmittance % |
| B1 | 1400 | 6.06 | 99.7 | 0.49 | 1400 | 6.08 | 0.49 | 1766 | 40 |
| B2 | 1600 | 6.06 | 99.7 | 1.45 | 1250 | 6.08 | 1.45 | 1058 | 43 |
| B3 | 1400 | 6.06 | 99.7 | 0.49 | 1250 | 6.08 | 0.49 | 1762 | 37 |

(Sample Production)

A uniaxial press and a mold were used to apply a pressure of 70 MPa to each raw-material powder to obtain platy moldings each having dimensions of 40 mm×50 mm and a thickness of 5 mm. These moldings each were put in a rubber mold and pressed with a cold isostatic press at a pressure of 200 MPa to consolidate the moldings. The consolidated moldings were sintered in the air at temperatures in the range of 1,100-1,500° C. for 2 hours to obtain sintered bodies. The densities of the sintered bodies thus obtained were determined by the Archimedes method.

(Results of Measurement)

The results of the sintered body density measurement are shown in Table 4.

TABLE 4

| | | | Alumina | | YAG | | Mullite | | Spinel | | Aluminum borate ($Al_2O_3 \cdot nB_2O_3$) | | |
|---|---|---|---|---|---|---|---|---|---|---|---|---|---|
| Kind of aid | | | $Al_2O_3$ | | $Al_2O_3 \cdot 3/5Y_2O_3$ | | $Al_2O_3 \cdot 2/3SiO_2$ | | $Al_2O_3 \cdot MgO$ | | n = ½ | n = 1 | n = 2 |
| Addition amount | mol % | | 0.31 | | 0.31 | | 0.31 | | 0.31 | | 0.31 | 0.31 | 0.31 |
| | wt % | | 0.25 | | 0.58 | | 0.40 | | 0.35 | | 0.08 | 0.17 | 0.34 |
| Sintering temperature (° C.) | 1500 | C1 | 6.07 99.8 | D1 | 6.06 99.6 | E1 | 5.99 98.6 | F1 | 6.06 99.7 | G1 | 6.07 99.8 | 6.07 I1 99.8 | 6.06 99.7 |
| | 1400 | C2 | 6.06 99.7 | D2 | 6.06 99.7 | E2 | 6.02 99.0 | F2 | 6.06 99.7 | G2 | 6.07 H2 99.8 | 6.06 I2 99.8 | 6.06 99.7 |
| Left-side symbols in each column are sample numbers. | 1300 | C3 | 6.05 99.5 | D3 | 6.04 99.4 | E3 | 5.97 98.2 | F3 | 6.05 99.4 | G3 | 6.07 H3 99.8 | 6.07 I3 99.9 | 6.08 100.0 |
| | 1250 | C4 | 5.91 97.2 | D4 | 5.87 96.5 | E4 | 5.62 92.4 | F4 | 5.93 97.5 | G4 | 6.07 H4 99.8 | 6.07 I4 99.8 | 6.07 99.8 |
| Upper row: g/cm³ | 1200 | C5 | 5.59 91.9 | D5 | 5.42 89.1 | E5 | 4.99 82.1 | F5 | 5.82 95.7 | G5 | 6.04 H5 99.3 | 6.06 I5 99.7 | 6.07 99.8 |
| Lower row: relative density, % | 1100 | C6 | 3.67 60.3 | D6 | 3.59 59.1 | E6 | 3.60 59.2 | F6 | 3.88 63.8 | G6 | 4.34 H6 71.5 | 4.38 I6 72.0 | 4.52 74.4 |

Figure 2A:
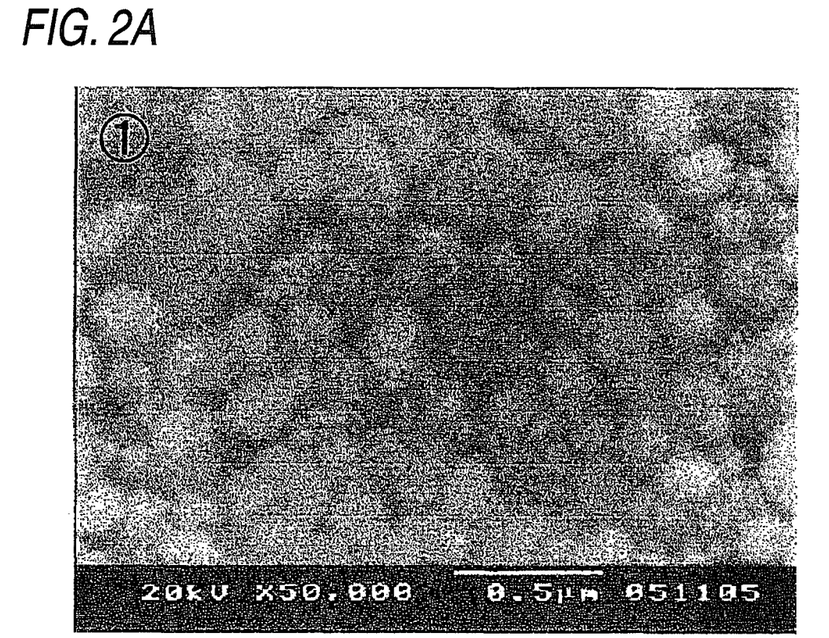
FIG. 2A is a view of an SEM image of grains of a 1,300° C. sintered body containing 0.25 wt % alumina (Sample No. C3 in Table 4) according to the invention.
Figure 2B:
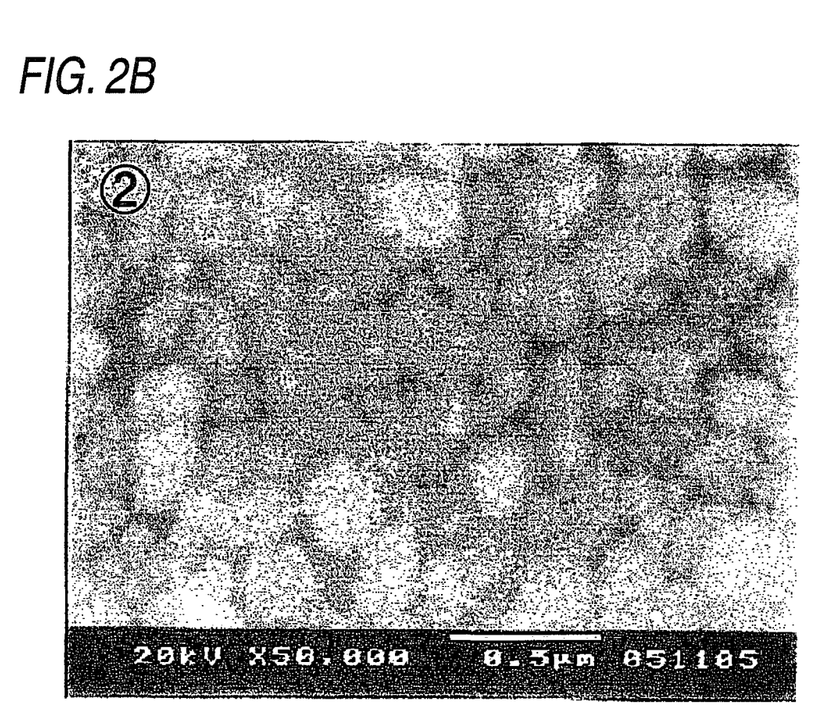
FIG. 2B is a view of an SEM image of grains of a 1,300° C. sintered body containing 0.35 wt % spinel (Sample No. F3 in Table 4) according to the invention.

The sintered bodies shown in Table 4 were examined with an SEM for grain size. SEM images of sintered body samples obtained through sintering at 1,300° C. are shown in FIG. 2A and FIG. 2B. The sample for which spinel had been added had a smaller grain size than the sample for which alumina had been added. The grain size of the sample for which 0.25 wt % alumina had been added was 0.3 µm, while that of the sample for which 0.35 wt % spinel had been added was about 0.25 µm.

Typical examples of the sintered bodies shown in Table 4 were used to obtain HIP sintered bodies, which were examined for density, average grain size, and strength and for total light transmittance at 0.5-mm thickness. The results of the measurements are shown in Table 5.

The HIP-treated sintered body thus obtained had a density of 6.08 g/cm³ (porosity, 0.15%), which was the same as that of sintered body plates obtained under the same conditions. The sintered body plates were examined for bending strength and total light transmittance. As a result, the average bending strength thereof was 1,950 MPa and the total light transmittance thereof as measured at 0.5-mm thickness was 45.2%.

The color tone of this part in a bracket shape also was not blackish, and the part was excellent in transparency and aesthetic properties.

EXAMPLE 51

A zirconia powder containing 5.0 mol % $Y_2O_3$ and having a specific surface area of 15 m²/g and a primary-crystal-grain

TABLE 5

| | Primary Sintered Body | | | | HIP Sintered Body | | | |
|---|---|---|---|---|---|---|---|---|
| Sample No. | Primary-sintering temperature ° C. | Density g/cm³ | Relative density % | Grain size µm | HIP temperature ° C. | Density$_{HIP}$ g/cm³ | Grain size$_{HIP}$ µm | Average bending strength MPa | Total light transmittance % |
| D4 | 1250 | 5.87 | 96.5 | 0.25 | 1500 | 6.08 | 0.6 | 1912 | 47 |
| F4 | 1250 | 5.93 | 97.5 | 0.20 | 1500 | 6.08 | 0.55 | 1905 | 46 |
| F5 | 1200 | 5.82 | 95.7 | 0.17 | 1500 | 6.08 | 0.55 | 1930 | 46 |

EXAMPLES 48 AND 49

A zirconia powder containing 2.5 mol % $Y_2O_3$ was prepared from a zirconia powder containing 3 mol % $Y_2O_3$ and having a specific surface area of 15.5 m²/g and a primary-crystal-grain size of 23 nm (TZ-3Y, manufactured by Tosoh Corp.) and a zirconia powder containing 2 mol % $Y_2O_3$ and having a specific surface area of 16.8 m²/g and a primary-crystal-grain size of 20 nm (TZ-2Y, manufactured by Tosoh Corp.). The two powders were added to each other in given amounts and mixed together in ethanol by means of a ball mill. The resultant mixture was vacuum-dried and disaggregated with a rotary evaporator to obtain a raw material. Furthermore, a zirconia powder containing 3.5 mol % $Y_2O_3$ was prepared in the same manner from the zirconia powder containing 3 mol % $Y_2O_3$ (TZ-3Y, manufactured by Tosoh Corp.) and a zirconia powder containing 4 mol % $Y_2O_3$ and having a specific surface area of 14.6 m²/g and a primary-crystal-grain size of 20 nm (TZ-4Y, manufactured by Tosoh Corp.).

Using these powders, sintered bodies were obtained in the same manner as in Example 1, except that the sintering for primary-sintered body production was conducted at a temperature of 1,350° C. and the HIP treatment was conducted at a temperature of 1,400° C. The sample containing 2.5 mol % $Y_2O_3$ had an average bending strength of 2,003 MPa and a total light transmittance of 44%. The sample containing 3.5 mol % $Y_2O_3$ had an average bending strength of 1,809 MPa and a total light transmittance at 0.5-mm thickness of 48.5%.

EXAMPLE 50

To 500 g of the TZ-3YE powder used in Example 1 was added 100 g of a thermoplastic wax resin. This mixture was kneaded with a heated kneader to obtain a compound. The compound was extruded with an injection molding machine to mold a bracket part shown in FIG. 3. This molding was degreased by heating to 900° C. and then sintered in the air at 1,350° C. for 2 hours. This sintered body was subjected to an HIP treatment in an argon gas medium by the same operating method as in Example 1 under the conditions of 1,500° C., 1 hour, and 150 MPa.

size of 30 nm (TZ-5Y, manufactured by Tosoh Corp.) was molded into a plate with a mold press and a rubber press. This plate was put in an electric furnace and held therein at 1,300° C. for 2 hours in the air to obtain a primary sintered body.

This primary sintered body had a density of 96.8% in terms of relative density (5.86 g/cm³) and an average crystal grain size of 0.37 µm. Subsequently, this primary sintered body was put in a vessel made of alumina, and a plate made of alumina was placed over the opening of the vessel to bring the inside of the vessel into a semi-sealed state. The primary sintered body in this vessel was subjected to HIP sintering for 1 hour in an argon gas atmosphere having a temperature of 1,350° C. and a pressure of 150 MPa. The sintered body obtained had a total light transmittance, as measured at 1-mm thickness, of 42%, contrast ratio of 57%, absorbing/scattering coefficient of 4.0 mm$^{-1}$, bending strength of 1,016 MPa, and fracture toughness of 4.0 MPa·m$^{0.5}$. The sintered body had an average crystal grain size of 0.49 µm. The crystal phases thereof consisted only of a fluorite type tetragonal crystal phase and a fluorite type cubic crystal phase, and the proportion of the fluorite type tetragonal crystal phase in the two crystal phases was 53.0%.

EXAMPLES 52 TO 55

The same raw-material powder as in Example 51 was molded. The resultant moldings were subjected to primary sintering and HIP sintering by the same method as in Example 51, except that the primary-sintering conditions and HIP sintering conditions were changed. The sintering conditions and properties of the sintered bodies obtained are shown in Tables 6 and 7.

EXAMPLE 56

A zirconia powder containing 6.0 mol % $Y_2O_3$ and having a specific surface area of 16 m²/g and a primary-crystal-grain size of 28 nm (TZ-6Y, manufactured by Tosoh Corp.) was molded into a plate with a mold press and a rubber press. This plate was put in an electric furnace and held therein at 1,300° C. for 2 hours in the air to obtain a primary sintered body.

This primary sintered body had a density of 98.9% in terms of relative density (5.96 g/cm³) and an average crystal grain size of 0.41 μm. Subsequently, this primary sintered body was put in a vessel made of alumina, and a plate made of alumina was placed over the opening of the vessel to bring the inside of the vessel into a semi-sealed state. The primary sintered body in this vessel was subjected to HIP sintering for 1 hour in an argon gas atmosphere having a temperature of 1,350° C. and a pressure of 150 MPa. The sintered body obtained had a total light transmittance, as measured at 1-mm thickness, of 44%, contrast ratio of 53%, absorbing/scattering coefficient of 2.9 mm$^{-1}$, and bending strength of 684 MPa. The sintered body had an average crystal grain size of 0.85 μm. The crystal phases thereof consisted only of a fluorite type tetragonal crystal phase and a fluorite type cubic crystal phase, and the proportion of the fluorite type tetragognal crystal phase in the two crystal phases was 36.4%.

EXAMPLES 57 TO 60

The same raw-material powder as in Example 56 was molded. The resultant moldings were subjected to primary sintering and HIP sintering by the same method as in Example 56, except that the primary-sintering conditions and HIP sintering conditions were changed as shown in Table 6. Properties of the sintered bodies obtained were evaluated, and the results obtained are shown in Table 7.

COMPARATIVE EXAMPLE 4

A zirconia powder containing 10.0 mol % $Y_2O_3$ (TZ-10Y, manufactured by Tosoh Corp.) was molded and sintered in the same manner as in Example 51, except that the sintering temperature was changed to 1,350° C. This sintered body was evaluated for properties. The sintering conditions are shown in Table 8, and the properties of the sintered body obtained are shown in Table 9.

The sintered body obtained had relatively high translucency because of the high $Y_2O_3$ concentration. However, the bending strength thereof was as low as 371 MPa, which was far lower than 500 MPa.

COMPARATIVE EXAMPLE 5

A zirconia powder containing 5.0 mol % $Y_2O_3$ (TZ-5Y, manufactured by Tosoh Corp.) was used as in Example 51 to produce a sintered body in the same manner as in Comparative Example 1, except that the HIP temperature was changed to 1,650° C. This sintered body was evaluated for properties. (See Tables 8 and 9).

The sintered body obtained had an average crystal grain size of 6.3 μm and relatively high translucency. However, the bending strength thereof was as low as 488 MPa. When a high HIP temperature was used and the sintered body obtained had a crystal grain size exceeding 5 μm, then this sintered body was unable to combine high strength and translucency.

TABLE 6

| | Primary-sintering conditions | | | | HIP sintering conditions | |
|---|---|---|---|---|---|---|
| No. | $Y_2O_3$ content (mol %) | Temperature (° C.) | Time (hr) | Relative density (%) | Temperature (° C.) | Pressure (MPa) |
| Example 51 | 5.0 | 1300 | 2 | 96.8 | 1350 | 150 |
| Example 52 | 5.0 | 1350 | 2 | 99.4 | 1350 | 150 |
| Example 53 | 5.0 | 1400 | 2 | 99.8 | 1350 | 150 |
| Example 54 | 5.0 | 1275 | 5 | 95.1 | 1500 | 150 |
| Example 55 | 5.0 | 1300 | 2 | 97.6 | 1400 | 150 |
| Example 56 | 6.0 | 1300 | 2 | 98.9 | 1350 | 150 |
| Example 57 | 6.0 | 1350 | 2 | 99.5 | 1350 | 150 |
| Example 58 | 6.0 | 1400 | 2 | 99.9 | 1350 | 150 |
| Example 59 | 6.0 | 1275 | 5 | 95.7 | 1350 | 150 |
| Example 60 | 6.0 | 1300 | 2 | 98.5 | 1400 | 150 |

TABLE 7

| No. | Relative density (%) | Crystal grain size (μm) | Total light transmittance 1 mm-t (%) | Contrast ratio (%) | Absorbing/ scattering coefficient (mm$^{-1}$) | Bending strength (MPa) | Fracture toughness MPa·m$^{0.5}$ |
|---|---|---|---|---|---|---|---|
| Example 51 | 99.98 | 0.49 | 42 | 57 | 4.0 | 1016 | 4.0 |
| Example 52 | 99.97 | 0.52 | 41 | 59 | — | 1122 | — |
| Example 53 | 99.98 | 0.55 | 41 | 59 | — | 1049 | — |
| Example 54 | 99.96 | 0.83 | 41 | 59 | — | 998 | 3.5 |
| Example 55 | 99.94 | 0.64 | 41 | 58 | — | 896 | — |
| Example 56 | 99.96 | 0.85 | 44 | 53 | 2.9 | 684 | — |
| Example 57 | 99.98 | 0.84 | 44 | 53 | — | 669 | — |
| Example 58 | 99.98 | 0.87 | 44 | 53 | — | 673 | — |
| Example 59 | 99.97 | 0.82 | 42 | 56 | 3.2 | 721 | — |
| Example 60 | 99.98 | 0.95 | 46 | 51 | — | 653 | — |

TABLE 8

| | Primary-sintering conditions | | | | HIP sintering conditions | |
|---|---|---|---|---|---|---|
| No. | $Y_2O_3$ content (mol %) | Temperature (° C.) | Time (hr) | Relative density (%) | Temperature (° C.) | Pressure (MPa) |
| Comparative Example 4 | 10 | 1350 | 2 | 99.2 | 1350 | 150 |
| Comparative Example 5 | 5 | 1400 | 2 | 99.8 | 1650 | 150 |

TABLE 9

| No. | Relative density (%) | Crystal grain size (μm) | Total light transmittance 1 mm-t (%) | Contrast ratio (%) | Absorbing/ scattering coefficient (mm$^{-1}$) | Bending strength (MPa) | Fracture toughness MPa·m$^{0.5}$ |
|---|---|---|---|---|---|---|---|
| Comparative Example 4 | 99.97 | 2.4 | 45 | 52 | — | 371 | 2.0 |
| Comparative Example 5 | 99.96 | 6.3 | 41 | 58 | — | 488 | — |

While the invention has been described in detail and with reference to specific embodiments thereof, it will be apparent to one skilled in the art that various changes and modifications can be made therein without departing from the spirit and scope thereof.

This application is based on a Japanese patent application filed on Jul. 25, 2006 (Application No. 2006-202261), Japanese patent application filed on Jan. 11, 2007 (Application No. 2007-003690), and Japanese patent application filed on Mar. 8, 2007 (Application No. 2007-058592), the contents thereof being herein incorporated by reference.

Industrial Applicability

The sintered bodies of the invention have not only high strength but also aesthetic properties based on translucency. The sintered bodies are hence applicable, of course, to mechanical/structural materials such as cutting tools, dies, nozzles, bearings, and rollers, and are especially effective as a material for artificial teeth or an orthodontic bracket which are utilized in the dental field. Consequently, the invention has a remarkable industrial value.

The invention claimed is:

1. A zirconia sintered body which comprises zirconia containing 2-4 mol % yttria and has a three-point bending strength of 1,700 MPa or higher and a total light transmittance, as measured at a thickness of 0.5 mm, of 43% or higher.

2. The zirconia sintered body according to claim 1, which has a three-point bending strength of 1,900 MPa or higher and a total light transmittance, as measured at a thickness of 0.5 mm, of 45% or higher.

3. The zirconia sintered body according to claim 1, characterized by being made of crystal phases which are constituted only of a fluorite structure tetragonal crystal phase (I) containing 3 mol % or less yttria or constituted of a mixed phase comprising a fluorite structure tetragonal crystal phase (I) containing 3 mol % or less yttria and a fluorite structure tetragonal crystal phase (II) containing 5 mol % or more yttria, the proportion of the fluorite structure tetragonal crystal phase (I) being 50-100%.

4. The zirconia sintered body according to claim 1, characterized by containing no voids of 10 μm or larger and having a porosity of 0.5% or lower.

5. A dental material comprising the zirconia sintered body according to claim 1.

6. An orthodontic bracket comprising the zirconia sintered body according to claim 1.

7. An artificial tooth comprising the zirconia sintered body according to claim 1.

8. A mill blank for dental materials which comprised the zirconia sintered body according to claim 1.

* * * * *